(12) United States Patent
Trieu

(10) Patent No.: US 7,578,849 B2
(45) Date of Patent: Aug. 25, 2009

(54) INTERVERTEBRAL IMPLANTS AND METHODS OF USE

(75) Inventor: Hai H. Trieu, Cordova, TN (US)

(73) Assignee: Warsaw Orthopedic, Inc.

( * ) Notice: Subject to any disclaimer, the term of this patent is extended or adjusted under 35 U.S.C. 154(b) by 125 days.

(21) Appl. No.: 11/340,972

(22) Filed: Jan. 27, 2006

(65) Prior Publication Data
US 2007/0191953 A1 Aug. 16, 2007

(51) Int. Cl.
*A61F 2/44* (2006.01)
(52) U.S. Cl. .................. 623/17.15; 623/17.13; 606/248
(58) Field of Classification Search .................. 606/61, 606/249, 279; 623/17.11–17.16
See application file for complete search history.

(56) References Cited

U.S. PATENT DOCUMENTS

| | | | |
|---|---|---|---|
| 4,743,260 A | 5/1988 | Burton | |
| 5,092,866 A | 3/1992 | Breard et al. | |
| 5,180,393 A | 1/1993 | Commarmond | |
| 5,282,863 A | 2/1994 | Burton | |
| 5,375,823 A | 12/1994 | Navas | |
| 5,415,661 A | 5/1995 | Holmes | |
| 5,423,816 A | 6/1995 | Lin | |
| 5,458,642 A | 10/1995 | Beer et al. | |
| 5,480,401 A | 1/1996 | Navas | |
| 5,540,688 A | 7/1996 | Navas | |
| 5,562,737 A | 10/1996 | Graf | |
| 5,584,834 A | 12/1996 | Errico et al. | |
| 5,645,599 A * | 7/1997 | Samani | 623/17.16 |
| 5,672,175 A | 9/1997 | Martin | |
| 5,676,702 A * | 10/1997 | Ratron | 623/17.16 |
| 5,702,450 A * | 12/1997 | Bisserie | 623/17.16 |
| 5,704,936 A | 1/1998 | Mazel | |
| 5,713,899 A | 2/1998 | Mamay et al. | |
| 5,733,284 A | 3/1998 | Martin | |

(Continued)

FOREIGN PATENT DOCUMENTS

DE 43 15 757 C1 11/1994

(Continued)

OTHER PUBLICATIONS

Trieu, Hai H., "Interspinous Devices and Methods of Use." filed Jan. 27, 2006, 31 pages, U.S. Appl. No. 11/341,200.

(Continued)

*Primary Examiner*—Thomas C Barrett
*Assistant Examiner*—Andrew Yang

(57) ABSTRACT

Implants and methods for spacing and stabilizing vertebral members. The implant in one embodiment may include first and second endplates and an intermediate section that form an interior section. An elastic member may be positioned within the interior section to space apart the endplates. The elastic member may have a variety of orientations, sizes, shapes, densities, modulus of elasticity, and other material properties depending upon the desired displacement between the first and second endplates. In use according to one embodiment, the implant may assume a first shape when the vertebral members are aligned, such as when the patient is standing erect or in a prone position. This first shape may include the first and second endplates spaced a first distance apart. During movement of the vertebral members, the endplates may be forced together. The intermediate section in combination with the elastic member may be deformed during this movement and thereby exert a force to stabilize the vertebral members.

18 Claims, 7 Drawing Sheets

U.S. PATENT DOCUMENTS

| | | |
|---|---|---|
| 5,749,916 A | 5/1998 | Richelsoph |
| 5,836,948 A | 11/1998 | Zucherman et al. |
| 5,928,284 A | 7/1999 | Mehidizadeh |
| 5,961,516 A | 10/1999 | Graf |
| 5,993,448 A | 11/1999 | Remmler |
| 6,231,609 B1 | 5/2001 | Mehdizadeh |
| 6,241,730 B1 | 6/2001 | Alby |
| 6,248,106 B1 | 6/2001 | Ferree |
| 6,267,764 B1 | 7/2001 | Elberg |
| 6,293,949 B1 | 9/2001 | Justis et al. |
| 6,296,643 B1 | 10/2001 | Hopf et al. |
| 6,387,134 B1 * | 5/2002 | Parker et al. ............... 623/55 |
| 6,402,750 B1 | 6/2002 | Atkinson et al. |
| 6,419,706 B1 * | 7/2002 | Graf ..................... 623/17.16 |
| 6,440,169 B1 | 8/2002 | Elberg et al. |
| 6,478,796 B2 | 11/2002 | Zucherman et al. |
| 6,514,256 B2 | 2/2003 | Zucherman |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,616,669 B2 | 9/2003 | Ogilvie et al. |
| 6,626,904 B1 | 9/2003 | Jamm et al. |
| 6,626,944 B1 | 9/2003 | Taylor |
| 6,645,207 B2 | 11/2003 | Dixon et al. |
| 6,706,044 B2 | 3/2004 | Kuslich et al. |
| 6,733,534 B2 | 5/2004 | Sherman |
| 6,743,257 B2 | 6/2004 | Castro |
| 6,783,527 B2 | 8/2004 | Drewry et al. |
| 6,793,679 B2 | 9/2004 | Michelson |
| 6,796,983 B1 | 9/2004 | Zucherman et al. |
| 6,835,205 B2 | 12/2004 | Atkinson et al. |
| 6,893,466 B2 | 5/2005 | Trieu |
| 6,966,910 B2 * | 11/2005 | Ritland ..................... 606/61 |
| 6,986,771 B2 | 1/2006 | Paul et al. |
| 6,989,011 B2 | 1/2006 | Paul et al. |
| 6,991,632 B2 | 1/2006 | Ritland |
| 7,018,379 B2 | 3/2006 | Drewry et al. |
| 7,029,475 B2 | 4/2006 | Panjabi |
| 7,066,957 B2 | 6/2006 | Graf |
| 7,083,621 B2 | 8/2006 | Shaolian et al. |
| 7,083,622 B2 | 8/2006 | Simonson |
| 7,125,410 B2 | 10/2006 | Freudiger |
| 7,137,985 B2 | 11/2006 | Jahng |
| 7,156,848 B2 * | 1/2007 | Ferree ..................... 606/61 |
| 7,291,150 B2 | 11/2007 | Graf |
| 7,326,210 B2 | 2/2008 | Jahng et al. |
| 7,329,258 B2 | 2/2008 | Studer |
| 7,338,525 B2 | 3/2008 | Ferree |
| 7,361,196 B2 | 4/2008 | Fallin et al. |
| 7,377,921 B2 | 5/2008 | Studer et al. |
| 2001/0007073 A1 | 7/2001 | Zucherman et al. |
| 2002/0077702 A1 * | 6/2002 | Castro ................ 623/17.16 |
| 2002/0133155 A1 | 9/2002 | Ferree |
| 2003/0109880 A1 | 6/2003 | Shirado et al. |
| 2003/0114853 A1 | 6/2003 | Burgess et al. |
| 2003/0171749 A1 | 9/2003 | Le Couedic et al. |
| 2003/0191470 A1 | 10/2003 | Ritland |
| 2003/0220643 A1 | 11/2003 | Ferree |
| 2004/0002708 A1 | 1/2004 | Ritland |
| 2004/0006343 A1 | 1/2004 | Sevrain |
| 2004/0049189 A1 | 3/2004 | Le Couedic et al. |
| 2004/0049190 A1 | 3/2004 | Biedermann et al. |
| 2004/0073215 A1 * | 4/2004 | Carli ..................... 606/61 |
| 2004/0106995 A1 | 6/2004 | Le Couedic et al. |
| 2004/0143264 A1 | 7/2004 | McAfee |
| 2004/0147928 A1 | 7/2004 | Landry et al. |
| 2004/0186570 A1 * | 9/2004 | Rapp ..................... 623/17.11 |
| 2004/0215191 A1 | 10/2004 | Kitchen |
| 2004/0236329 A1 | 11/2004 | Panjabi |
| 2004/0243239 A1 | 12/2004 | Taylor |
| 2004/0267260 A1 | 12/2004 | Mack et al. |
| 2005/0043796 A1 | 2/2005 | Grant et al. |
| 2005/0049708 A1 | 3/2005 | Atkinson |
| 2005/0065516 A1 | 3/2005 | Jahng |
| 2005/0085815 A1 | 4/2005 | Harms |
| 2005/0113927 A1 | 5/2005 | Malek |
| 2005/0124991 A1 | 6/2005 | Jahng |
| 2005/0125063 A1 | 6/2005 | Matge et al. |
| 2005/0131407 A1 | 6/2005 | Sicvol et al. |
| 2005/0143737 A1 | 6/2005 | Pafford et al. |
| 2005/0143823 A1 | 6/2005 | Boyd et al. |
| 2005/0143827 A1 | 6/2005 | Globerman et al. |
| 2005/0149020 A1 | 7/2005 | Jahng |
| 2005/0149023 A1 | 7/2005 | Ritland |
| 2005/0154390 A1 | 7/2005 | Biedermann et al. |
| 2005/0165396 A1 | 7/2005 | Fortin et al. |
| 2005/0171540 A1 | 8/2005 | Lim |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0203513 A1 | 9/2005 | Jahng et al. |
| 2005/0203514 A1 | 9/2005 | Jahng et al. |
| 2005/0203518 A1 | 9/2005 | Biedermann et al. |
| 2005/0203519 A1 | 9/2005 | Harms et al. |
| 2005/0203624 A1 * | 9/2005 | Serhan et al. ............ 623/17.11 |
| 2005/0209694 A1 | 9/2005 | Loeb |
| 2005/0222569 A1 | 10/2005 | Panjabi |
| 2005/0261685 A1 | 11/2005 | Fortin et al. |
| 2005/0261686 A1 | 11/2005 | Paul |
| 2005/0261768 A1 | 11/2005 | Trieu |
| 2005/0277922 A1 | 12/2005 | Trieu |
| 2005/0277934 A1 | 12/2005 | Vardiman |
| 2005/0288670 A1 | 12/2005 | Panjabi et al. |
| 2005/0288672 A1 | 12/2005 | Ferree |
| 2006/0009768 A1 | 1/2006 | Ritland |
| 2006/0036240 A1 | 2/2006 | Colleran et al. |
| 2006/0041259 A1 | 2/2006 | Paul et al. |
| 2006/0064090 A1 | 3/2006 | Park |
| 2006/0084982 A1 | 4/2006 | Kim |
| 2006/0084984 A1 | 4/2006 | Kim |
| 2006/0084987 A1 | 4/2006 | Kim |
| 2006/0084991 A1 | 4/2006 | Borgstrom et al. |
| 2006/0142758 A1 | 6/2006 | Petit |
| 2006/0142760 A1 | 6/2006 | McDonnell |
| 2006/0184171 A1 | 8/2006 | Biedermann et al. |
| 2006/0189985 A1 | 8/2006 | Lewis |
| 2006/0195093 A1 | 8/2006 | Jahng |
| 2006/0212033 A1 | 9/2006 | Rothman et al. |
| 2006/0229608 A1 | 10/2006 | Foster et al. |
| 2006/0229612 A1 | 10/2006 | Rothman et al. |
| 2006/0241765 A1 * | 10/2006 | Burn et al. ............ 623/17.12 |
| 2006/0247632 A1 | 11/2006 | Winslow et al. |
| 2006/0247637 A1 | 11/2006 | Colleran et al. |
| 2006/0264935 A1 | 11/2006 | White |
| 2006/0264937 A1 | 11/2006 | White |
| 2006/0276790 A1 | 12/2006 | Dawson et al. |
| 2006/0282080 A1 | 12/2006 | Albert et al. |
| 2006/0293657 A1 | 12/2006 | Hartmann |
| 2007/0016190 A1 | 1/2007 | Martinez et al. |
| 2007/0016193 A1 | 1/2007 | Ritland |
| 2007/0016200 A1 | 1/2007 | Jackson |
| 2007/0016201 A1 | 1/2007 | Freudiger |
| 2007/0043356 A1 | 2/2007 | Timm et al. |
| 2007/0049936 A1 | 3/2007 | Colleran et al. |
| 2007/0049937 A1 | 3/2007 | Matthis et al. |
| 2007/0055247 A1 | 3/2007 | Jahng |
| 2007/0073289 A1 | 3/2007 | Kwak et al. |
| 2007/0088359 A1 | 4/2007 | Woods et al. |
| 2007/0100341 A1 | 5/2007 | Reglos et al. |
| 2007/0123871 A1 | 5/2007 | Jahng |

| | | | | | | |
|---|---|---|---|---|---|---|
| 2007/0129729 A1 | 6/2007 | Petit et al. | | 2008/0154307 A1 | 6/2008 | Colleran et al. |
| 2007/0198088 A1 | 8/2007 | Biedermann et al. | | | | |
| 2007/0213719 A1 | 9/2007 | Hudgins et al. | | | | |
| 2007/0225710 A1 | 9/2007 | Jahng et al. | | | | |
| 2007/0233064 A1 | 10/2007 | Holt | | | | |
| 2007/0270860 A1 | 11/2007 | Jackson | | | | |
| 2007/0276380 A1 | 11/2007 | Jahng et al. | | | | |
| 2007/0288008 A1 | 12/2007 | Park | | | | |
| 2007/0288093 A1 | 12/2007 | Le Couedic et al. | | | | |
| 2007/0293862 A1 | 12/2007 | Jackson | | | | |
| 2008/0021459 A1 | 1/2008 | Lim | | | | |
| 2008/0033435 A1 | 2/2008 | Studer et al. | | | | |
| 2008/0039943 A1 | 2/2008 | Le Couedic | | | | |
| 2008/0045951 A1 | 2/2008 | Fanger et al. | | | | |
| 2008/0097431 A1 | 4/2008 | Vessa | | | | |
| 2008/0097434 A1 | 4/2008 | Moumene et al. | | | | |
| 2008/0140076 A1 | 6/2008 | Jackson | | | | |
| 2008/0147122 A1 | 6/2008 | Jackson | | | | |

FOREIGN PATENT DOCUMENTS

| | | |
|---|---|---|
| EP | 0 642 775 | 3/1995 |
| EP | 1 287 794 | 3/2003 |
| FR | 2 722 980 | 2/1996 |
| FR | 2 774 581 | 8/1999 |
| FR | 2 844 180 A1 | 12/2004 |
| FR | 2 860 428 | 4/2005 |
| WO | WO 01/62190 A1 | 8/2001 |
| WO | WO 02/102259 A2 | 12/2002 |
| WO | 2004/089244 | 10/2004 |
| WO | 2004/105577 | 12/2004 |
| WO | 2005-011522 | 2/2005 |
| WO | 2006/106246 | 10/2006 |

OTHER PUBLICATIONS

Trieu, Hai H., "Vertebral Rods and Methods of Use." filed Jan. 27, 2006, 32 pages, U.S. Appl. No. 11/340,973.

* cited by examiner

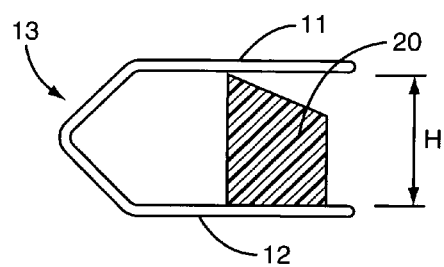 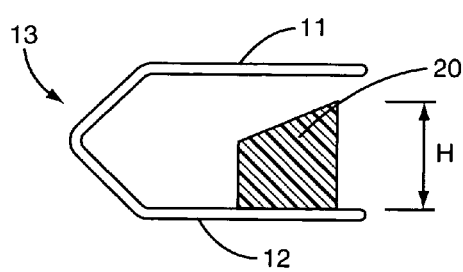
*FIG. 9A*  *FIG. 9B*
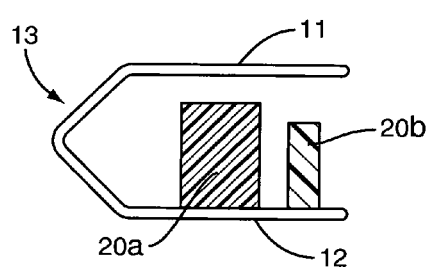 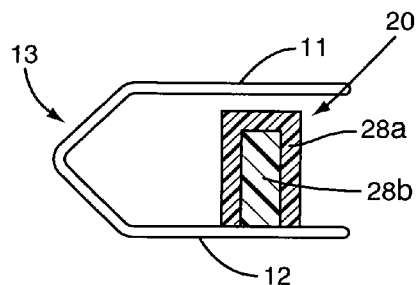
*FIG. 9C*  *FIG. 9D*
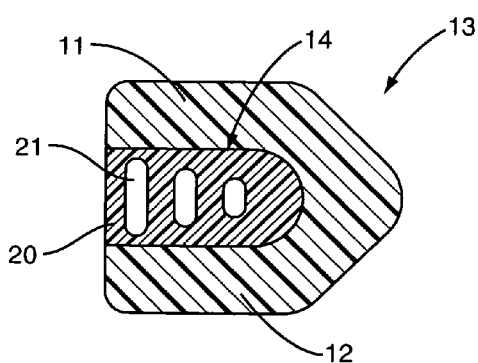 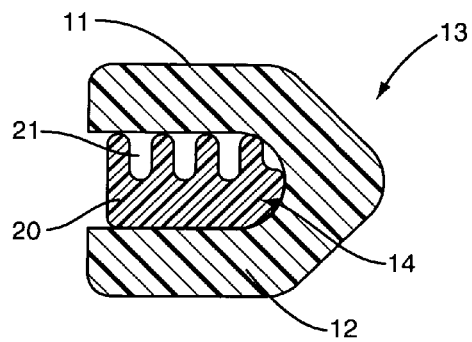
*FIG. 10*  *FIG. 11*

INTERVERTEBRAL IMPLANTS AND METHODS OF USE

BACKGROUND

The present application is directed to devices and methods for stabilizing vertebral members, and more particularly, to intervertebral implants and methods of use for replacing an intervertebral disc, vertebral member, or combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

SUMMARY

The present application is directed to implants and methods for spacing and stabilizing vertebral members. The implant may include first and second endplates and an intermediate section that form an interior section. An elastic member may be positioned within the interior section to space apart the endplates. The elastic member may have a variety of orientations, sizes, shapes, densities, modulus of elasticity, and other material properties depending upon the desired displacement between the first and second endplates.

In use according to one embodiment, the implant may assume a first shape when the vertebral members are aligned, such as when the patient is standing erect or in a prone position. This first shape may include the first and second endplates spaced a first distance apart. During movement of the vertebral members, the endplates may be forced together or apart. The intermediate section in combination with the elastic member may be deformed during this movement and thereby exert a force to stabilize the vertebral members.

BRIEF DESCRIPTION OF THE DRAWINGS

FIGS. 9A-9D are side schematic views of embodiments of elastic members positioned within a body.

FIG. 10 is a cross-sectional view of an elastic member according to one embodiment.

FIG. 11 is a cross-sectional view of an elastic member according to one embodiment.

DETAILED DESCRIPTION

The present application is directed to implants and methods for replacing an intervertebral disc, vertebral member, or combination of both. The implant includes a body sized to replace the removed elements. The body may include first and second endplates and an intermediate section that together form an interior section. An elastic member is positioned within the interior section. The elastic member may have a variety of orientations, sizes, shapes, densities, modulus of elasticity, and other material properties depending upon the desired displacement between the first and second endplates. The endplates may be spaced apart a first distance when the vertebral members are aligned. During movement of the vertebral members, the endplates may be forced together or apart. The intermediate section in combination with the elastic member may be deformed during this movement and thereby exert a force that prevents or reduces the movement of the endplates.

Figure 1:
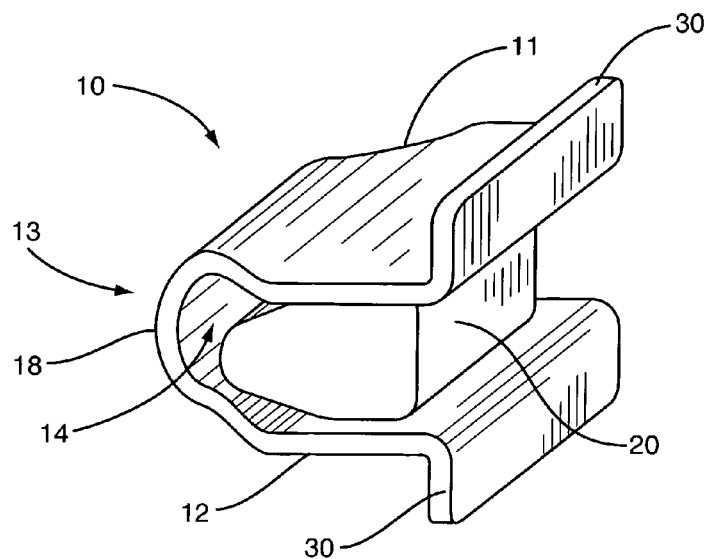
FIG. 1 is a perspective view of an implant according to one embodiment.

FIG. 1 illustrates one embodiment of an implant having a body 10. Body 10 includes an upper endplate 11, lower endplate 12, and an intermediate section 13. Intermediate section 13 spaces apart the endplates 11, 12 forming an interior section 14. An elastic member 20 is positioned within the interior section 14. Tabs 30 may extend from the body 10 and provide a means for positioning the body 10 relative to the vertebral members 100.

Figure 2:
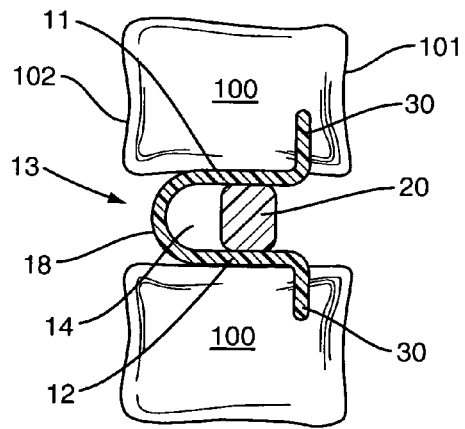
FIG. 2 is a cross-sectional view of an implant positioned between vertebral members according to one embodiment.

FIG. 2 illustrates a cross-sectional view of the implant of FIG. 1 positioned within the patient. The implant is in a first position with the vertebral members 100 being substantially aligned. The upper and lower endplates 11, 12 are in contact with vertebral members 100. Intermediate section 13 is positioned within the space formed between the vertebral members 100. In this embodiment, intermediate section 13 is positioned in a posterior direction in proximity with a posterior edge 102 of the vertebral members and away from an anterior edge 101. Elastic member 20 is positioned within the interior section 14. Tabs 30 extend into the vertebral members 100 to position the implant.

Figure 3:
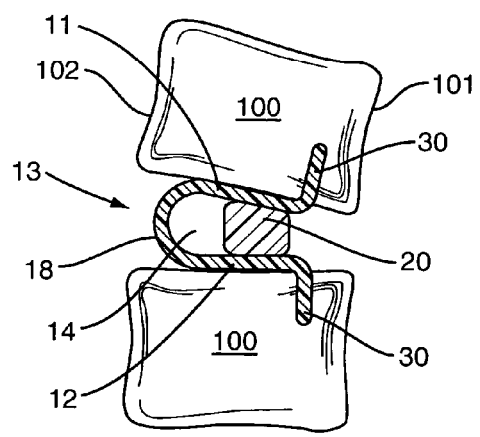
FIG. 3 is a cross-sectional view of an implant positioned between vertebral members that are in flexion according to one embodiment.

FIG. 3 illustrates the implant with the vertebral members 100 in flexion. The movement of the vertebral members 100 causes the endplates 11, 12 to move inward towards one another and elastically deform the elastic member 20 and the intermediate section 13. The intermediate section 13 and the elastic member 20 resist the flexion and apply an outward force on the vertebral members 100. The amount of force applied to the vertebral members 100 may vary as described below in detail. Both the intermediate section 13 and elastic member 20 may be constructed of elastic, resilient materials that return towards their original shape upon realignment of the vertebral members 100

In one embodiment, the intermediate section 13 and the elastic member 20 are flexible to provide dynamic stabilization while maintaining certain biomechanical motions of the spine. Stabilization may be maintained during motions such as flexion, extension, lateral bending, and rotation. The intermediate section 13 and elastic member 20 are constructed to have a predetermined stiffness to provide the stabilization. Further, the stiffness may vary during a biomechanical motion.

Figure 5:
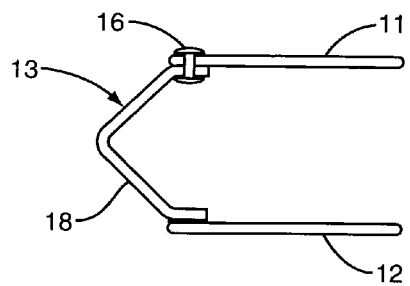
FIG. 5 is a side schematic view of a body according to one embodiment.
Figure 7:
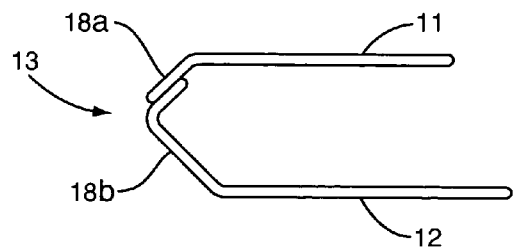
FIG. 7 is a side schematic view of a body according to one embodiment.

Body 10 comprises the upper and lower endplates 11, 12 and the intermediate section 13. In one embodiment such as illustrated in FIG. 1, the body 10 is constructed of a single member having a folded configuration. In other embodiment, body 10 is constructed of two or more different members. FIG. 5 illustrates one embodiment with the intermediate section 13 constructed of a separate piece that is attached to the endplates 11, 12. Upper endplate 11 is attached to the member 18 with one or more fasteners 16. Embodiments of fasteners 16 may include rivets, pins, screws, etc. Lower endplate 12 is attached to the member 18 in another manner, such as with adhesives, welding, brazing, etc. FIG. 7 illustrates another embodiment with the intermediate section 13 constructed of two separate members 18a, 18b. In this embodiment, first member 18a is integral with endplate 11, and second member 18b is integral with endplate 12. Members 18a, 18b are connected together in a manner as described above. Body 10 may be constructed of a variety of materials including metals, polymers, ceramics, and combinations thereof. Examples of metals include titanium, titanium alloys such as nickel-titanium, stainless steel, and cobalt chromium. Examples of polymers include PEEK, PEEK-carbon composites, polyimide, polyetherimide, and polyurethane. Examples of ceramics include calcium phosphate, hydroxyapatite, HAPCP, alumina, and zirconium.

Figure 14A:
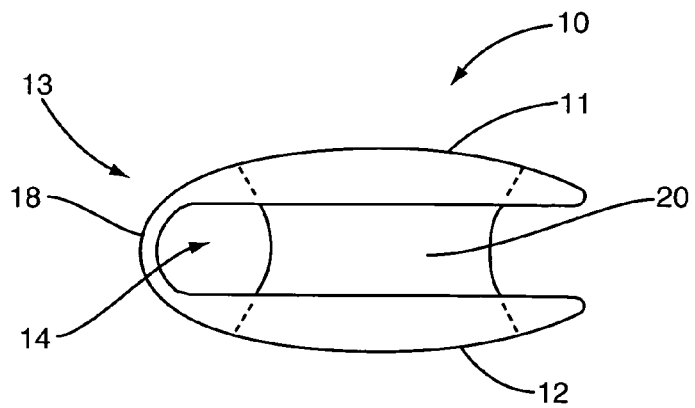
FIGS. 14A-C are views of an implant according to one embodiment.
Figure 14B:
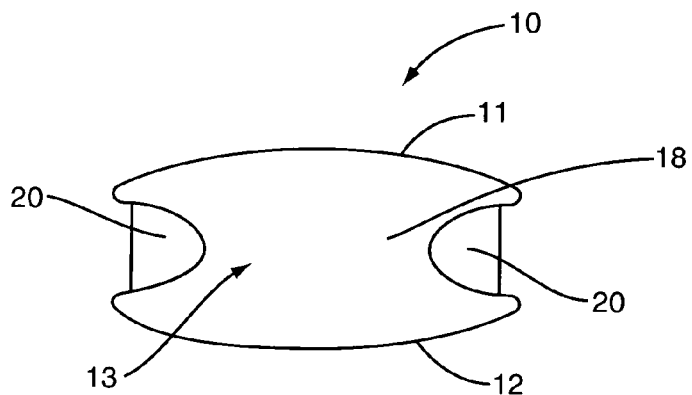

Endplates 11, 12 are shaped to contact the vertebral members 100. Endplates 11, 12 may be shaped to adapt accurately to the shape of the plates of the vertebral members 100. The shape and size of the endplates 11, 12 may vary, as well as the size of the surface area that contacts the vertebral members 100. One embodiment illustrated in FIGS. 14A-C includes convex endplates 11, 12. The upper and lower endplates 11, 12 may have the same shape and size, or may have different shapes or sizes. By way of example, the embodiment of FIG. 1 includes endplates 11, 12 having substantially the same shape and size. In other embodiments, endplates 11, 12 may have different shapes and sizes. Examples of shapes for the endplates 11, 12 include round, oval, elliptical, kidney shaped, square, rectangular, trapezoidal, and boomerang shape, etc.

Figure 4:
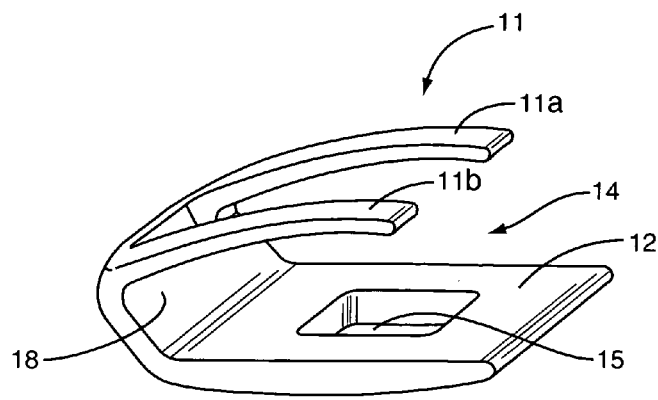
FIG. 4 is a perspective view of a body having upper and lower endplates and an intermediate section according to one embodiment.
Figure 6A:
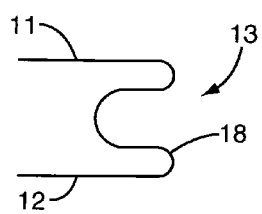
FIGS. 6A-F are side schematic views of embodiments of a body with an intermediate section.
Figure 6B:
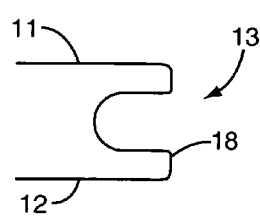
Figure 6C:
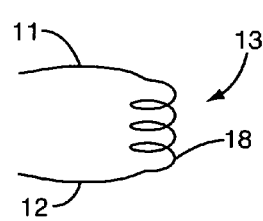
Figure 6D:
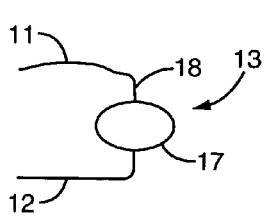
Figure 6E:
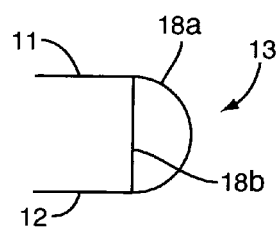
Figure 6F:
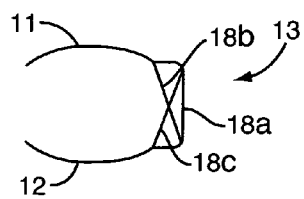

One embodiment illustrated in FIG. 4 includes the upper endplate 11 with a split configuration having first and second fingers 11a, 11b, with the lower endplate 12 formed as a single section and having an opening 15. In one embodiment, the space formed between the fingers 11a, 11b and the opening 15 are aligned. In one embodiment, endplates 11, 12 have a planar construction as illustrated in the embodiments of FIGS. 4, 6A, and 6B. In another embodiment, endplates 11, 12 have a curved construction as illustrated in the embodiments of FIGS. 6C, and 6F. In yet other embodiments, endplates 11, 12 have a combination of curved and planar sections as illustrated in the embodiment of FIG. 6D.

Endplates 11, 12 may be positioned at a variety of relative angular positions when no external forces are applied to the implant. In one embodiment, endplates 11, 12 are substantially parallel. In another embodiment, the endplates 11, 12 angle outward from the intermediate section 13 such that a height of the interior section 13 is less near the intermediate section 13 and increases towards the ends of the endplates 11, 12. In another embodiment, endplates 11, 12 angle inward as they extend from the intermediate section 13.

Figure 8A:
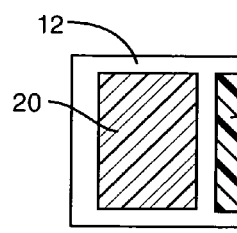
FIGS. 8A-8H are cross-sectional top views of embodiments of an elastic member positioned relative to an endplate.
Figure 8B:
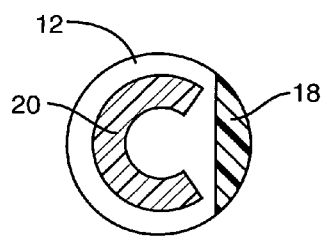
Figure 8C:
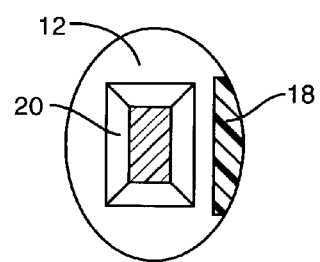
Figure 8D:
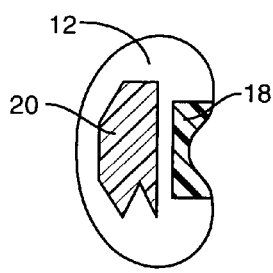
Figure 8E:
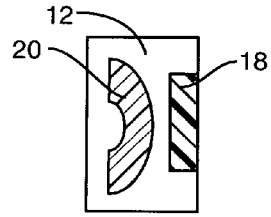
Figure 8F:
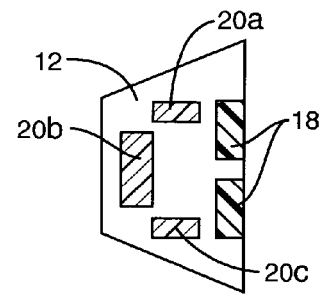
Figure 8G:
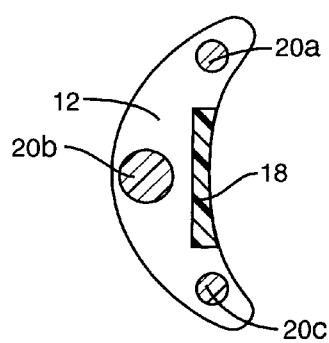
Figure 8H:
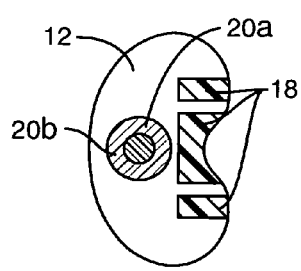

Intermediate section 13 extends between the endplates 11, 12 and provides resistance to movement of the endplates 11, 12. Intermediate section 13 may have a variety of shapes. In one embodiment as illustrated in FIG. 5, intermediate section 13 has substantially planar upper and lower sections. In other embodiments, intermediate section 13 has a curved shape. In various other embodiments, intermediate section 13 has a combination of planar and curved shapes. The width of the intermediate section 13 may be substantially the same or different as one or both endplates 11, 12. In one embodiment illustrated in FIGS. 14A-C, the width of the intermediate section 13 is less than the endplates 11, 12. The narrower width may be centered along a centerline of the body 10, or may be off-center. The thickness of the intermediate section 13 may be the same or different as one or both endplates 11, 12. In one embodiment, intermediate section 13 comprises two separate spaced-apart sections as illustrated in FIG. 8H.

In some embodiments, intermediate section 13 is constructed from a single member 18. FIG. 6A illustrates one embodiment with the intermediate section 13 having a curved shape with an overlapping configuration between the endplates 11, 12. FIG. 6B illustrates an embodiment having an intermediate section 13 with an overlapping configuration and comprised of planar and curved sections. FIG. 6C illustrates an embodiment having multiple overlapping sections. FIG. 6D illustrates an embodiment with an intermediate section 13 having an enclosed section 17 positioned between sections of member 18.

Figure 14C:
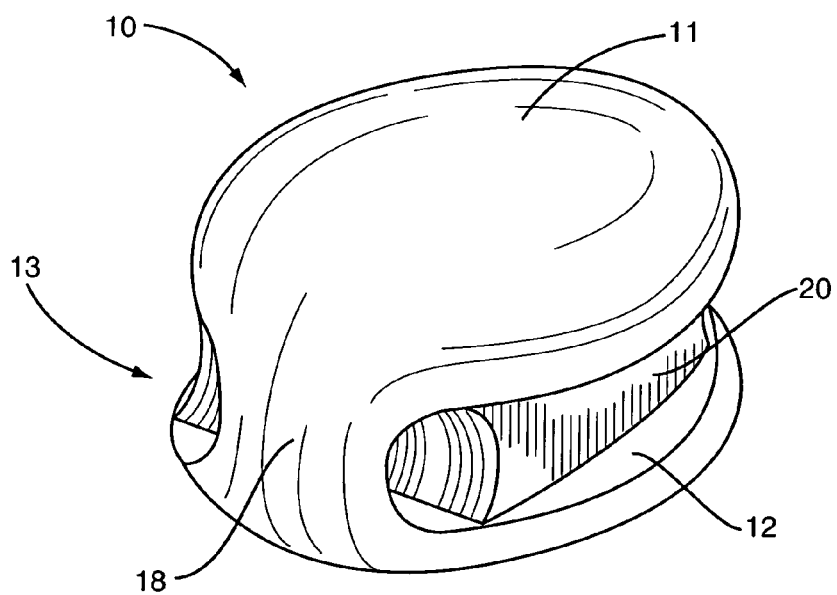

Embodiments of the intermediate section 13 may include multiple members 18. FIG. 6E illustrates an embodiment with a curved first support section 18a and a second support section 18b. FIG. 6F illustrates another embodiment of an intermediate section 13 comprising sections 18a, 18b, and 18c. Section 18a extends from the endplates 11, 12. Sections 18b, 18c form a criss-cross pattern. In embodiments having multiple members 18, members 18 may be constructed in a unitary fashion, or from multiple different members fastened together. Members 18 may extend along the entire width of the endplates 11, 12, or a limited section or sections of the width. In the embodiment of FIG. 4, the endplate 18 extends along substantially the entire width. In the embodiment of FIG. 14C, the member 18 extends along a limited width of the endplates 11, 12. Further, the body may include multiple members 18 as illustrated in the embodiments of FIGS. 8F and 8H. In embodiments with multiple members 18, the members may have the same construction, or may have different constructions.

Elastic member 20 is positioned within the interior space 14 and has a stiffness to provide resistance and prevent movement of the endplates 11, 12. The elastic member 20 shares the load applied to the implant and may prevent fatigue failure of the intermediate section 13. The elastic member 20 may impose a substantially linear or non-linear resistance to prevent movement of the endplates 11, 12.

Elastic member 20 may be constructed of a variety of different materials. Member 20 may be resilient and change shape during movement of the endplates 11, 12. Examples of such materials include elastic or rubbery polymers, hydrogels or other hydrophilic polymers, or composites thereof. Particularly suitable elastomers include silicone, polyurethane, copolymers of silicone and polyurethane, polyolefins, such as polyisobutylene and polyisoprene, neoprene, nitrile, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include polyvinyl alcohol hydrogel, polyacrylamide hydrogel, polyacrylic hydrogel, poly(N-vinyl-2-pyrrolidone hydrogel, polyhydroxyethyl methacrylate hydrogel, and naturally occurring materials such as collagen and polysaccharides, such as hyaluronic acid and cross-linked carboxyl-containing polysaccharides, and combinations thereof.

Elastic member 20 may be connected to the body 10, or may be freely positioned within the interior section 14. In one embodiment, elastic member 20 is connected to one or more of the endplates 11, 12 and intermediate section 13. The elastic member 20 may be connected with mechanical fasteners such as screws, pins, rivets, etc. In another embodiment, elastic member 20 is connected to the body 10 with an adhesive. In one embodiment, the inner edges of one or more of the endplates 11, 12 and intermediate section 13 include a roughened surface, ridges, teeth, etc. to maintain the position of the elastic member 20. In one embodiment, the elastic member 20 is shaped to connected with one or both endplates 11, 12. In a specific embodiment, the elastic member 20 has a dovetailed recess that mounts to an extension that extends from the endplate.

When connected to both endplates 11, 12, the elastic member 20 provides resistance to both inward and outward movement. During inward movement of the endplates 11, 12, elastic member 20 is compressed and provides a resistance to the inward movement. During outward movement of the endplates 11, 12, the elastic member 20 is placed in tension to provide resistance. In one embodiment, the elastic member 20 is placed in compression during flexion of the vertebral members and placed in tension during extension.

In one embodiment with the elastic member 20 connected to only one endplate 11 or 12, or when positioned between the endplates 11, 12 and connected to neither, the elastic member 20 provides resistance to inward movement. The elastic member 20 may not be placed in tension during outward movement and the resistance to this movement is limited to the intermediate section 13.

Elastic member 20 may be spaced from or in contact with the intermediate section 13. Elastic member 20 may further have a variety of heights and widths. In various embodiments, elastic member 20 is constructed from a single member as illustrated in FIGS. 8A-8E. FIG. 8A illustrates one embodiment having an elastic member 20 with a substantially rectangular shape. FIG. 8B illustrates a substantially C-shaped elastic member 20 with the base facing an anterior direction away from the support member 18 of the intermediate section 13. FIG. 8C illustrates an elastic member 20 having a rectangular first surface that contacts the endplate 12 and four planar sidewalls that taper upwards. FIG. 8D illustrates an embodiment having an irregular, non-symmetrical shape. FIG. 8E illustrates an embodiment having a substantially C-shaped elastic member 20 with a base facing in a posterior direction towards the support member 18 of the intermediate section 13.

Elastic member 20 may further include two or more separate members. The separate members may have the same construction, or may be constructed of different materials having a different stiffness. FIG. 8F illustrates an embodiment having three separate elastic members 20a, 20b, 20c. Each elastic member 20a, 20b, 20c is independent and positioned within the interior section 14 and has a substantially rectangular shape. FIG. 8G illustrates another embodiment having elastic members 20a, 20b, 20c each having a circular cross-sectional shape. FIG. 8H illustrates an embodiment having a first elastic member 20a that is positioned within a second elastic member 20b. In one embodiment, elastic members 20a, 20b are connected together. In embodiments as illustrated in FIGS. 8G and 8H, elastic members 20 may have cylindrical, spherical, or conical shapes.

In a non-deformed state, the elastic member 20 may have a variety of heights H. In one embodiment, the height is sized for the member 20 to extend between and contact both endplates 11, 12. In one embodiment, the height H may be substantially the same throughout the elastic member 20. In other embodiments as illustrated in FIGS. 9A and 9B, the height H may vary along the elastic member 20. In one embodiment, elastic member 20 has a first height H when the vertebral members are aligned. When placed in compression, the elastic member 20 has a smaller height. When placed in tension, the elastic member 20 stretches and has a greater height.

FIG. 9A includes elastic member 20 having a height that decreases away from the intermediate section 13, and FIG. 9B includes the elastic member 20 having a height the increases away from the intermediate section 13.

The implant may provide a variable resistance to deformation. The variable resistance may cause less resistance to initial amounts of vertebral movement, but apply greater forces to reduce larger vertebral movements. By way of example, the implant may be designed to provide little resistance during an initial amount of movement of the endplates 11, 12. Larger amounts of resistance may be applied to the vertebral members when the endplates 11, 12 move beyond the initial amount. In some embodiments, the stiffness of the elastic member 20 and intermediate section 13 increases with additional amounts of movement. The amount of resistance applied by one or both members may increase the further they move away from the original, first position.

Variable resistance may also result during compression from the height of the elastic member 20. In one embodiment, the height of the elastic member 20 is less than the height of the interior section (i.e., the member 20 does not contact both endplates 11, 12). The resistance to the initial inward movement of the endplates 11, 12 is isolated to the intermediate section 13. The elastic member 20 does not affect the stiffness until it is contacted by both endplates 11, 12 and begins to deform. In one embodiment, deformation is limited to the intermediate section 13 during an amount of initial endplate movement. Movement beyond this initial amount causes the endplates 11, 12 to begin deforming the elastic member 20 in addition to continued deformation of the intermediate section 13 resulting in greater stiffness of the implant and more resistance to additional movement.

The shape of the elastic member 20 may further cause variable resistance to deformation. Greater amounts of contact between the endplates 11, 12 and the elastic member 20 may result in greater amounts of resistance. By way of example using the embodiments of FIGS. 9A and 9B, the peaked shapes of the elastic members 20 provides less resistance during initial amounts of inward movement of the endplates 11, 12. Additional inward movement of the endplates 11, 12 results in deformation of larger amounts of the elastic member 20 resulting in greater resistance.

Variable resistance may also be provided by multiple elastic elements. FIG. 9C illustrates an embodiment having two separate elastic members 20a and 20b. During inward movement of the endplates 11, 12, the inner elastic member 20a is initially contacted thus causing a first amount of resistance. The second elastic member 20b is not contacted by the endplate 11 until the endplates 11, 12 are compressed beyond a predetermined amount. This compression then causes the elastic member 20b to deform resulting in additional amounts of resistance. In this embodiment, elastic members 20a, 20b may have the same or different stiffnesses.

FIG. 9D illustrates an embodiment having a single elastic member 20 constructed of first and second materials 28a, 28b having a different stiffness. Initial compression of the endplates 11, 12 causes deformation of the first material 28a resulting in a first resistance. Additional compression causes deformation of the first and second materials 28a, 28b which together provide additional resistance.

In another embodiment (not illustrated), first and second members 20a, 20b are each attached to both endplates 11, 12. In this embodiment, the first member 20a has a greater height than the second member 20b. During initial outward movement of the endplates 11, 12, the second member 20b is placed in tension before the first member 20a. After a predetermined amount of outward movement, the first member 20a is also placed in tension thus increasing the overall resistance to movement of the endplates 11, 12.

Elastic member 20 may fill varying amounts of the interior section 14. As illustrated in the embodiments of FIG. 2, member 20 fills a limited amount of the interior section 14. In another embodiment as illustrated in FIGS. 10 and 11, elastic members 20 substantially fill the entirety of the interior section 14. In the embodiments of FIGS. 10 and 11, voids 21 are positioned within the elastic member 20. In one embodiment, voids have a specific shape and size to control the supporting abilities of the elastic member 20. Voids 21 may be substantially free of material, or may be filled with a material that is different than that of the elastic member 20. As illustrated in FIG. 10, voids 21 may be positioned within the interior of the elastic member 20, or may be positioned along one edge as illustrated in FIG. 11.

In one embodiment, elastic member 20 is positioned completely within the interior section 14. In other embodiments, elastic member 20 is positioned within the interior section 14 and extends outward from one or more sides.

Figure 12:
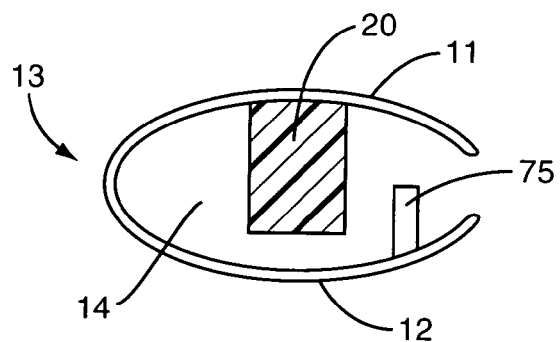
FIG. 12 is a schematic side view of a limiter according to one embodiment.

A limiter may prevent movement of the endplates 11, 12 beyond a predetermined amount. FIG. 12 illustrates one embodiment having a rigid limiting member 75 positioned within the interior section 14. Inward movement of the endplates 11, 12 will cause deformation of the elastic member 20. At a predetermined amount of movement, a top edge of limiting member 75 contacts the endplate 11 and prevents further inward movement. Limiting member 75 may have a variety of different shapes and orientations. In another embodiment, limiting member 75 is formed of a non-elastic member that is attached to both endplates 11, 12. The limiting member 75 is in a slackened condition during an initial orientation as a length of the member 75 is greater than the distance between the endplates 11, 12. After the endplates 11, 12 have moved outward a predetermined distance, the limiting member 75 is tightened and limits further outward movement.

Figure 13A:
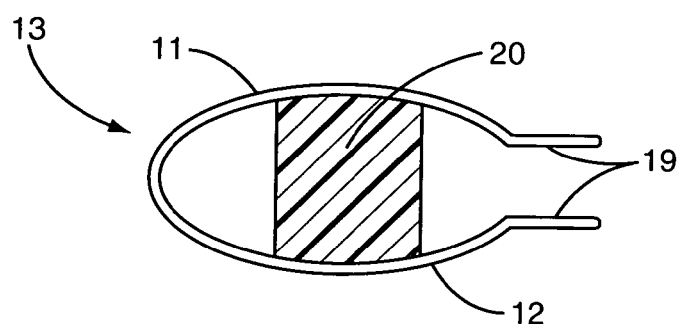
FIGS. 13A-13B are side schematic views of a limiter according to one embodiment.
Figure 13B:
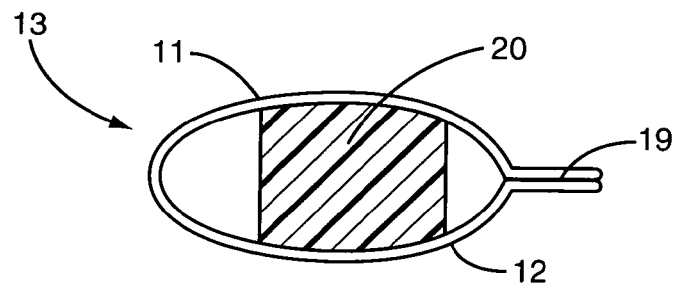

Another limiting embodiment is illustrated in FIGS. 13A and 13B. Endplates 11, 12 are formed with ends 19 positioned opposite from the intermediate section 13. In a first position as illustrated in FIG. 13A, ends 19 are spaced apart. This allows for inward movement of the endplates 11, 12 during vertebral movement. At a predetermined amount of inward movement, ends 19 contact together as illustrated in FIG. 13B and further inward movement is prevented.

In one embodiment, a keel extends outward from one or both endplates 11, 12 to connect with the vertebral members 100. In one embodiment as illustrated in FIG. 2, tabs 30 are positioned within the vertebral members 100. In another embodiment, tabs 30 are positioned along an outer edge of the vertebral members 100 with the interior section 14 and intermediate section 13 positioned between the vertebral members 100. Tabs 30 may include apertures for receiving fasteners to attach the implant to the vertebral members 100.

In one embodiment, one or both endplates 11, 12 are constructed to have increased contact with the vertebral members. In one embodiment, the endplates 11, 12 are constructed of a porous material. In another embodiment, endplates 11, 12 are textured. In still other embodiments, endplates 11, 12 include spikes or serrations. In one embodiment, one or both endplates 11, 12 may be coated with osteo-conductive material. Embodiments of the material may include hydroxyapatite and BMP.

Vertebral movement may cause relative movement of the endplates 11, 12. The terms "inward movement", "outward movment" and the like are used herein in a general sense to describe the general motion of the endplates 11, 12 that reduces or increases the distance between the endplates 11, 12. The endplates 11, 12 may move directly towards or away from one another during this movement, or there may be some lateral component to the movement. Further, the vertebral movement may cause movement of one or both of the endplates 11, 12.

The device can be placed within the intervertebral space by a variety of different approaches including anterior and lateral approaches. In one embodiment the device is inserted through a posterior approach.

Figure 15:
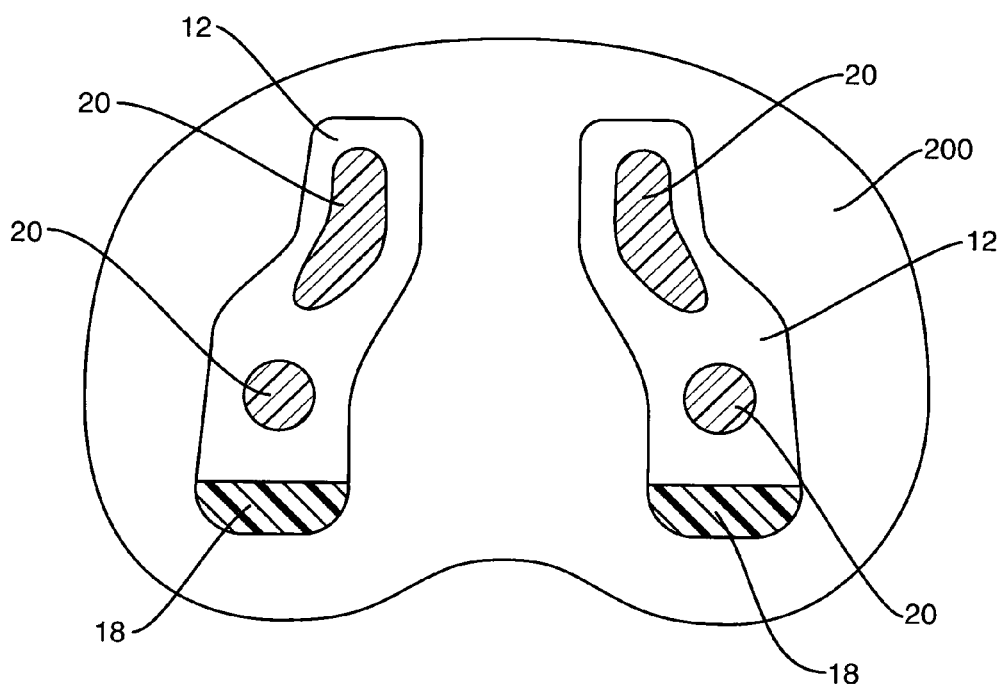
FIG. 15 is a cross-sectional top view of devices positioned relative to a vertebral member according to one embodiment.

In one embodiment, multiple devices are inserted within the intervertebral space as illustrated in FIG. 15. In this embodiment, the devices may be placed bilaterally with the intervertebral space relative to the vertebral member 200.

In another embodiment, a single device is inserted for the correction of scoliosis. In this embodiment, the device may be placed on the concaved side of the spinal column to increase the disc height on the lower side.

In one embodiment, the elastic member 20 is positioned within the interior section 14 prior to placing the implant into the intervertebral space. In another embodiment, the body 10 is initially placed within the intervertebral space and then the elastic member 20 is positioned within the interior section 14.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

Spatially relative terms such as "under", "below", "lower", "over", "upper", "lower", "intermediate", and the like, are used for ease of description to explain the relative positioning of elements. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

The present invention may be carried out in other specific ways than those herein set forth without departing from the scope and essential characteristics of the invention. In one embodiment, the implant replaces all or a part of a disc. In another embodiment, implant replaces all or part of a disc and all or part of one or more vertebral members. Intermediate section 13 may have the same width as the endplates 11, 12, or may have different widths. Intermediate section 13 may also have the same or different thickness as the endplates 11, 12. The present embodiments are, therefore, to be considered in all respects as illustrative and not restrictive, and all changes coming within the meaning and equivalency range of the appended claims are intended to be embraced therein.

What is claimed is:

1. An intervertebral device configured to be positioned between vertebral members, the device comprising:
    an elongated member having an overlapping configuration defining a first and a second endplate and an intermediate section, the first and second endplates being spaced apart by the intermediate section to form an interior space with open lateral sides and an interior height, the intermediate section including a folded configuration with at least three overlapping vertical sections;
    an elastic member spaced apart from the intermediate section and positioned between the first and second endplates such that the elastic member is spaced apart from one of the first and second endplates, the elastic member including a height less than the interior height and greater than at least one-half of the interior height, the elastic member being sized to space apart the first and second endplates during movement of the vertebral members;
    the elastic member includes a first section with a first stiffness and a second section with a second greater stiffness, the elastic member arranged such that the first section deforms upon a first amount of movement of the first and second endplates, and the first and second sections both deform upon a second greater amount of movement of the first and second endplates.

2. The device of claim 1, wherein the first endplate has a different shape than the second endplate.

3. The device of claim 2, wherein the first endplate comprises first and second spaced-apart fingers that form an opening in communication with the interior space.

4. The device of claim 1, wherein the intermediate section and the first and second endplates form a substantially C-shape.

5. The device of claim 1, wherein the intermediate section comprises first and second support members.

6. The device of claim 1, wherein the elastic member is spaced away from the intermediate section.

7. The device of claim 1, further comprising a second elastic member positioned between the first and second endplates, the second elastic member being spaced away from the elastic member.

8. The device of claim 7, wherein the second elastic member has a different stiffness than the elastic member.

9. The device of claim 7, wherein the second elastic member has a different height than the elastic member.

10. The device of claim 1, further comprising a limiting member positioned between the first and second endplates, the limiting member being constructed to limit movement of the first and second endplates beyond a predetermined amount.

11. The device of claim 1, wherein the elastic member has a length measured between a first edge and a second edge, a height of the elastic member being variable along the length.

12. An intervertebral device configured to be positioned between vertebral members, the device comprising:
    a flexible body having a width and positioned in an overlapping configuration to define a three-sided cavity, the cavity including an interior height; and
    the flexible body including an intermediate section spaced apart from the elastic member, the intermediate section including a folded configuration with at least three overlapping vertical sections when the device is positioned between the vertebral members;
    an elastic member positioned within the cavity and sized to space apart first and second sections of the flexible body, the elastic member includes a height less than the interior height such that the elastic member is spaced apart from one of the first and second sections such that the body deforms to reduce the interior height a predetermined amount before compressing the elastic member, and the elastic member spaced apart from the intermediate section;
    the elastic member including a first material with a first stiffness and a second material with a second different stiffness, the elastic member positioned relative to the first and second endplates with the first material being deformed prior to the second material during a decrease in the interior height.

13. The device of claim 12, further comprising a second elastic member positioned within the cavity.

14. The device of claim 12, further comprising a limiter positioned within the cavity, the limiter being constructed to prevent first and second endplates of the flexible body from moving beyond a predetermined limit.

15. The device of claim 12, wherein a height of the elastic member varies along the length of the elastic member.

16. An intervertebral device configured to be positioned between vertebral members, the device comprising:
    an elastic member; a first endplate positioned above the elastic member and a second endplate positioned below the elastic member, the elastic member in contact with one of the first and second endplates and spaced apart from the other of the first and second endplates;
    an intermediate member integral with the first and second endplates and positioned at ends of the first and second endplates and forming a cavity with open lateral sides, the intermediate member being deformable to allow the other of the first and second endplates to contact the elastic member and to apply a force to the elastic member during movement of the vertebral members, the intermediate member includes an overlapping configuration with at least three overlapping vertical sections when the device is positioned between the vertebral members; and
    a second elastic member positioned between the endplates and including a different stiffness than the elastic member;
    the first and second endplates and the intermediate member forming a three sided cavity sized to receive the elastic member;
    a height of the first elastic member being at least one-half of a height of an interior space formed between the first and second endplates when the device is in an undeformed state;
    an opening formed through one of the first and second endplates, the opening extending into the cavity.

17. The device of claim 16, wherein the elastic member extends outward beyond the first and second endplates.

18. The device of claim 16, wherein the elastic member has a variable height.

* * * * *